United States Patent [19]
Stoll et al.

[11] Patent Number: 5,681,982
[45] Date of Patent: Oct. 28, 1997

[54] PROBE FOR EVALUATING SEAFLOOR GEOACOUSTIC AND GEOTECHNICAL PROPERTIES

[75] Inventors: Robert D. Stoll, Demarest, N.J.; Tuncay Akal, La Spezia, Italy

[73] Assignee: The Trustees of Columbia University in the City of New York, New York, N.Y.

[21] Appl. No.: 551,519

[22] Filed: Nov. 1, 1995

[51] Int. Cl.$^6$ .................................................. G01N 3/00
[52] U.S. Cl. ............................ 73/12.13; 73/84; 73/12.04
[58] Field of Search .............................. 73/84, 85, 12.01, 73/12.04, 12.06, 12.13; 367/4, 15

[56] References Cited

U.S. PATENT DOCUMENTS

| | | | |
|---|---|---|---|
| 3,298,222 | 1/1967 | Costello et al. | |
| 3,455,151 | 7/1969 | Richard | 73/84 |
| 3,534,605 | 10/1970 | Koning et al. | 73/84 |
| 4,007,633 | 2/1977 | Thompson | |
| 4,492,111 | 1/1985 | Kirkland | 73/85 |
| 4,593,895 | 6/1986 | Cyr et al. | 73/12.13 |

OTHER PUBLICATIONS

Sippican Brochure, Sippican, Inc., Seven Barnabas Road, Marion, MA 02738.

ASTM Standard Test Method D3441-86 "Deep, Quasi-Static, Cone and Friction-Cone Penetration Tests of Soils," Annual Book of ASTM Standards, vol. 04.08, Soil & Rock; Building Stones; Geotextiles, Dec. 1986.

Robertson, P. K. and Campanella, R. G. (1983), "Interpretation of Cone Penetration Tests, Part II: Clay," Can. Geotech. J., 20 pp. 734–745 (excerpt), Month–NA, not available.

Senneset, K. and Janbu, N. (1985), "Shear Strength Parameters Obtained from Static Cone Penetration Tests," in *Strength Testing of Marine Sediments, Laboratory and In–Situ Measurements*, eds. R. Chaney and K. Demars, ASTM Spec. Tech. Publ. No. 883, pp. 41–54, Month–NA, not available.

Dayal, U. and Allen, J. H., "The Effect of Penetration Rate on the Strength of Remolded Clay and Sand Samples," Canadian Geotechnical Journal, v. 12, pp. 336–348 (1975), Month–NA, not available.

Novak, M. and Beredugo, Y.O. (1972), "Vertical Vibration of Embedded Footings," J. Soil Mech. and Found. Div. ASCE, 98, No. SM12, pp. 1291–1310 (excerpt), Dec. 1972.

Baranov, V. A. (1967), "On the Calculation of Excited Vibrations of an Embedded Foundation" (in Russian) Voprosy Dynamiki i Prochnocti, No. 14, Polytechnical Institute of Riga, pp. 195–209, Month Not available.

Lamb, H. (1904), "On the Propagation of Tremors Over the Surface of An Elastic Solid," Philosoph. Trans. Royal Soc., London, Ser. A, 203, pp. 1–42, Jan. 1, 1904.

Sonatech Brochure, Sonatech, Inc., 879 Ward Drive, Santa Barbara, CA 93111, date–Not available.

Sippican Brochure, Sippican, Inc., Seven Barnabas Road, Marion, MA 02738, date–Not available.

(List continued on next page.)

*Primary Examiner*—Ronald L. Biegel
*Attorney, Agent, or Firm*—Brumbaugh, Graves, Donohue & Raymond

[57] ABSTRACT

An apparatus and method is disclosed for determining geotechnical and geoacoustic properties of seafloor sediment wherein the undrained shear strength and dynamic shear modulus of such sediments can be quantified. Features of the deceleration profile of a seafloor penetrometer are compared to a data base of known insitu properties of seafloor sediments to determine a correlation between the features of the deceleration profile, such as maximum deceleration or jerk, and the seafloor sediment undrained shear strength. The damped oscillatory portion of the penetrometer deceleration profile, which occurs after plastic deformation and further permanent penetration into the sediments ends, is analyzed to determine the dominant or resonant frequency of the oscillations. This dominant frequency can be used to determine the seafloor sediment dynamic shear modulus.

35 Claims, 6 Drawing Sheets

OTHER PUBLICATIONS

Schmid, W., "Penetration of Objects into the Ocean Bottom" (1969) (Final Report Excerpt) Mar. 1969.

Robertson R. M., "Expendable Instrumentation," GM Defense Laboratories Report (1965) Month–not available.

Chari, T. R., Smith, W. G. and Zielinski, A., "Use of Free Fall Penetrometer in Sea Floor Engineering," Memorial University of Newfoundland, pre–1980, Date–not available.

Reece, E. W. and Stoller, H. M., "The Development of Multifunctional Seafloor Instrumentation Systems," Sandia Laboratories, pre–1978, Date–Not available.

U.S. patent application No. 06/399,512 filed Jul. 19, 1982 by Ingram.

R.M. Beard, "Expendable Doppler Penetrometer for Deep Ocean Sediment Measurements," Strength Testing of Marine Sediments: Laboratory and In–Situ Measurements, ASTM STP 883, 1985 pp. 101–124 1985, No month avail.

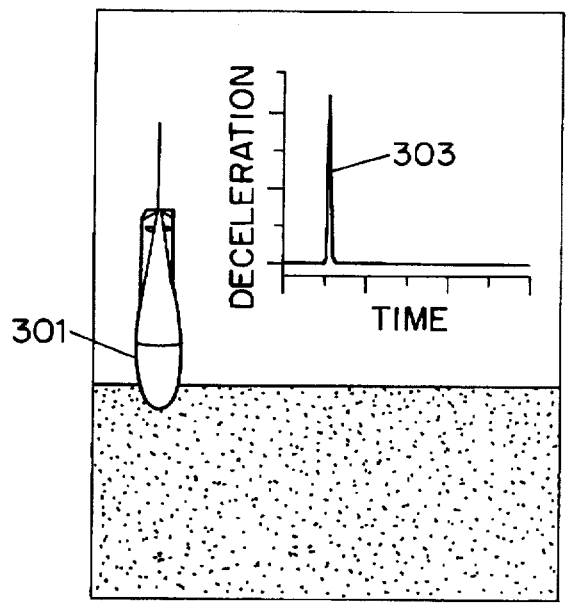
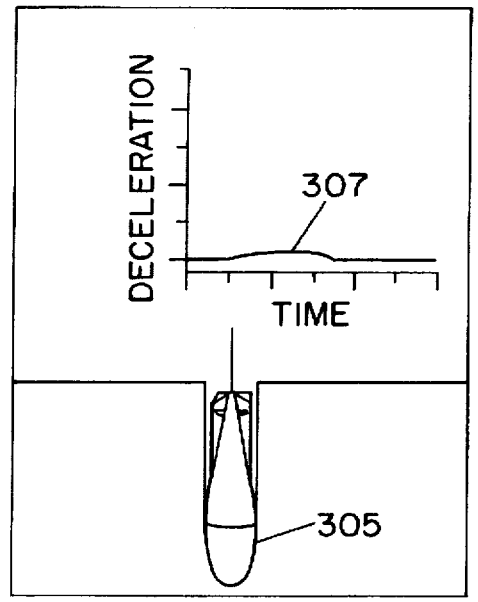
FIG. 3A — GRANULAR MATERIAL (DILATION)
FIG. 3B — PLASTIC MATERIAL (UNDRAINED SHEAR)
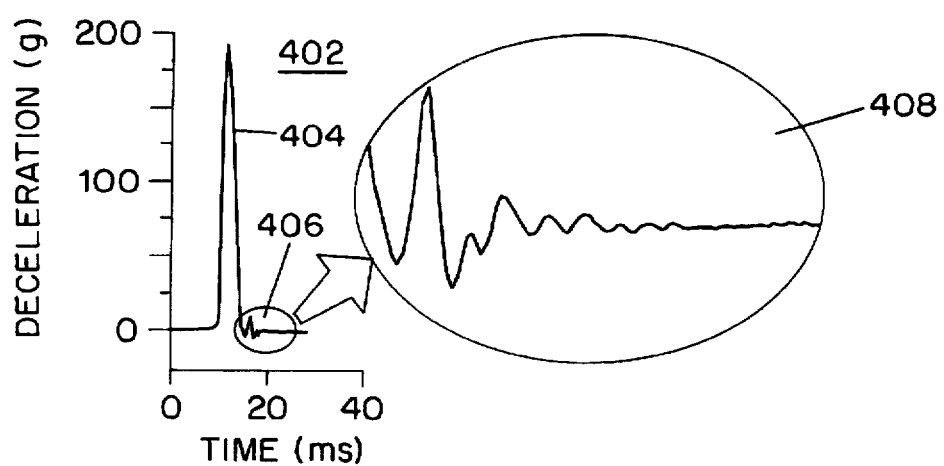
FIG. 4

PROBE FOR EVALUATING SEAFLOOR GEOACOUSTIC AND GEOTECHNICAL PROPERTIES

The U.S. Government has a paid-up license in this invention and the right in limited circumstances to require the patent owner to license others on reasonable terms as provided for by the terms of Grant No. N00014-94-1-0258 awarded by the Office of Naval Research.

The invention relates to a seafloor penetrometer which may be used to classify geoacoustic and geotechnical properties of seafloor sediments. More particularly, the invention relates to an apparatus and method for determining the undrained shear strength and dynamic shear modulus of seafloor sediments using a dynamic seafloor penetrometer.

BACKGROUND OF THE INVENTION

Penetrometers of various kinds, including both dynamic and quasi-static varieties, have been used for many years to probe soils and ocean sediments in an effort to evaluate the mechanical properties of these materials. An example of the quasi-static variety is the standard cone penetration test specified by the American Society for Testing and Materials (ASTM) wherein a rod with a 60 degree conical tip and a cross-sectional area of 10 square centimeters is pushed into the soil or sediment at the rate of 2 cm/sec. See ASTM Standard Test Method D3441-86 "Deep, Quasi-Static, Cone and Friction-Cone Penetration Tests of Soils." Annual Book of ASTM Standards, Vol. 04.08, Soil & Rock; Building Stones; Geotextiles. Under these conditions, the axial force on the tip gives an indication of the shearing strength of the material as a function of the depth of penetration.

Interpretation of the data resulting from such tests depends on whether the sediment being penetrated is a fine-grained, cohesive material of low permeability such as clay, or a granular material of much higher permeability such as a beach sand. In the case of the clay, the penetration resistance is directly related by plasticity theory to a fundamental property of the material called "undrained shear strength." In a granular material, the penetration resistance depends on the state of intergranular stress, or effective stress, and a parameter called the "angle of internal friction." In the case of the granular material, what is actually being measured is the drained shear strength owing to the fact that the rate of penetration of a typical probe is slow enough to allow dissipation of any excess pore-water pressure that begins to develop as a result of the tendency of granular soil to dilate when sheared at high levels of strain.

There is a large body of information in the geotechnical engineering literature wherein penetration resistance has been correlated with undrained shear strength or angle of internal friction taking into account a variety of influencing factors such as stress history and relative density. See, for example, Robertson and Campanella (1983) "Interpretation of Cone Penetration Tests, Part II: Clay," Can. Geotech. J., 20 pp. 734–745, and Senneset and Janbu (1985) "Shear Strength Parameters Obtained from Static Cone Penetration Tests," in *Strength Testing of Marine Sediments, Laboratory and In-Situ Measurements*, eds. R. Chaney and K. Demars, ASTM Spec. Tech. Publ. No. 883, pp. 41–54.

The notion of using a dynamic penetrometer to measure the properties of ocean sediments as well as soil deposits on land dates back to the 1960's. During the period from the late 1960's to the early 1980's there was a flurry of activity in this area. Many devices designed to measure deceleration, velocity and/or force during penetration were introduced and a few were patented (see, e.g., Costello et al., U.S. Pat. No. 3,298,222, January 1967 and Thompson, U.S. Pat. No. 4,007,633, February 1977). These devices ranged from those involving high velocity projectiles, some of which were actually fired from a gun into the seafloor, to systems where accelerometers or other motion sensing transducers were coupled to conventional sampling devices that penetrate the bottom, such as gravity corers.

The only device that has successfully evolved from this early work to the point where it is commercially available is a penetrometer whose motion is tracked using an acoustic signal and doppler-shift technology. These units are able to penetrate significant distances into many softer sediments because of their size and weight, however, they are very expensive and there is some question as to how well they can resolve conditions very near the water-sediment interface. The doppler-shift penetrometers are currently available through Sonatech, Inc. of Santa Barbara, Calif. for approximately $3,000.00 per unit.

Other early work on dynamic penetrometers utilized accelerometers as the transducing element and interpreted results based on simple empirical algorithms that were used to classify the sediments into crude categories such as "mud", "soft clay", etc. See, for example, U.S. patent application Ser. No. 06/399,512, filed Jul. 19, 1982 by Ingram. No effort was made in such work, however, to reliably extract numerical values for basic parameters such as quasi-static undrained shear strength. Moreover, none of this earlier work recognized or addressed the possibility of obtaining small-strain parameters such as dynamic shear modulus by using the complete deceleration profile of the impact. The present invention discloses an apparatus and method for quantifying these parameters.

In fine-grained water-saturated sediments, such as those found on the seafloor, the undrained shear strength is the principal parameter that determines the short term bearing capacity of the bottom. The bearing capacity is a measure of the maximum force that an object such as a mine, an anchor or a structural footing can impose on the surface of the sediment before large vertical displacement occurs. It is one of the main parameters needed by the navy in mine counter measures evaluation and is also important in a wide range of other applications such as offshore foundation design, slope stability studies, cable laying operations, and other applications known to those skilled in the art.

The dynamic shear modulus is a parameter that determines the velocity of propagation of seismic shear waves in a sediment. The value of this parameter together with a knowledge of the compressional wave speed is necessary in order to formulate a geoacoustic model of the seafloor that can predict the response for a variety of different kinds of wave motion. Such a geoacoustic model is important to the navy in studies of long range sound propagation in the water column and seafloor, to seismologists in studies of earthquake waves and to the oil industry in various techniques of seismic exploration. Other such applications will be known to those skilled in the art.

In dynamic tests, where a freely falling probe or other kind of penetrometer penetrates the sediment at a rapid rate, undrained response may be measured for both granular and cohesive materials. The resistance measured in the cohesive materials by dynamic probes, however, is different than for the case where the penetration rate is very low because of strain rate effects. For example in cohesive sediments, going from the low strain rates associated with the plastic deformation that occurs during the quasi-static ASTM test described above to high strain rates that will occur when a probe penetrates the sediment at velocities of, say, 6 or 7 meters/sec, will cause a 40 to 50% increase in penetration resistance based on theoretical considerations and laboratory tests. Hence, to derive quasi-static, undrained shear strength, from dynamic tests, this strain rate effect must be known.

Much of the data on strain rate effect currently in the literature, however, is based on laboratory tests which often utilize reconstituted samples of sediment which may not fully replicate insitu conditions. See, for example, Dayal and Allen, "The Effect of Penetration Rate on the Strength of Remolded Clay and Sand Samples," Canadian Geotechnical Journal, v. 12, pp. 336-348 (1975). Moreover, during penetration of a dynamic probe, the strain rate varies over a wide range as the penetrometer decelerates from the velocity at initial contact to zero at full penetration. Hence the magnitude of this effect must be established on the basis of insitu measurements using the actual probe configuration for which the strain rate effect must be evaluated.

In the case of dynamic tests on water-saturated, granular sediments, the mechanics of penetration resistance is significantly different than for the quasi-static case. When a rapidly moving probe impacts the surface of this kind of sediment, there is a sudden decrease in pore-water pressure in the zones where high shear stresses are generated near the circumference of the loaded area and as a result the mean intergranular stresses are also suddenly increased. This results in a short-term but marked increase in shear strength and therefore an attendant marked increase in penetration resistance. It has been found that this kind of response occurs in uniform granular sediments with a porosity less than about 45 or 50% because this defines the upper limit of the range of packing geometries that will result in dilative behavior.

At the time a dynamic probe begins penetration of a sediment, it's momentum is $m \cdot v_t$, where m is the mass of the probe and $v_t$ is the terminal or impact velocity. During penetration the force F(t) exerted on the sediment by the probe as a function of time t is related to the momentum at impact by $$m \cdot v_t = \int F(t)dt$$

As the probe penetrates the sediment, most of the kinetic energy available at contact ($\frac{1}{2} m v_t^2$) is converted into the work required to produce permanent plastic deformation. However, when the force exerted by the probe drops below the bearing capacity of the sediment, further permanent deformation ceases and the remaining energy results in damped, oscillatory motion of small amplitude. The frequency of such oscillatory motion depends on a number of factors such as the mass and diameter of the probe and the dynamic shear modulus of the sediment. The dynamic shear modulus, as noted above, is a small-strain parameter that relates oscillatory shear stress to shear strain and hence it, together with the total mass density, determines the velocity of seismic shear waves propagating in the sediment.

In view of the above, it can be seen that the force encountered by a dynamic probe F(t), depends on the type of sediment as well as a variety of other factors such as probe size and terminal velocity. Moreover, the full deceleration profile contains information not only pertaining to the shearing strength of the material but also to the dynamic shear modulus. The invention described herein is a combination system and data base designed to extract information on sediment type, undrained shear strength and dynamic shear modulus from the deceleration profile.

Accordingly, it is an object of this invention to extract and quantify geoacoustical and geotechnical parameters from seafloor sediments; particularly the undrained shear strength and dynamic shear modulus of such sediment.

It is a further object of this invention to extract such parameters based on comparisons with a database of known insitu properties of seafloor materials.

It is a further object of this invention to extract such parameters using expendable apparatus and methodology that is far less expensive than any alternative means to determine such seafloor parameters.

It is a further object of this invention to provide an apparatus with sufficient sensitivity over large dynamic range to allow accurate analysis of undrained shear strength and dynamic shear modulus.

Further objects and improvements of the invention will be apparent to those skilled in the art upon review of the preferred embodiment detailed below.

SUMMARY OF THE INVENTION

The invention consists of a matched system of components that includes a dynamic penetrometer for measurement of seafloor sediment properties utilizing an accelerometer as the principal transducer; a two or three wire data transmission system; an electronics system with characteristics that allow the full signature of the transducer to be analyzed to obtain (1) a classification as to whether the soil is granular or cohesive, (2) a numerical value of insitu undrained shear strength and (3) a numerical value for the insitu dynamic shear modulus; and a data base which yields the necessary factors that permit translation from transducer output to the insitu properties mentioned above. Because of its sensitivity and design, the disclosed apparatus is suited to the acquisition of detailed quantitative information regarding the geoacoustical and geotechnical properties of interest.

BRIEF DESCRIPTION OF THE DRAWINGS

FIG. 3 is an illustration of the physical penetration and resulting deceleration profile expected for dilative/granular sediments and cohesive/clay-like sediments, respectively.

FIG. 4 shows a typical deceleration profile/impact signature for a penetrometer entering seafloor sediments. The figure shows, in insert, the features of the damped oscillatory portion of the deceleration profile which occurs after plastic deformation of the seafloor sediment is completed.

DETAILED DESCRIPTION OF THE INVENTION

A preferred embodiment of the invention will now be described with reference to the attached FIGS. 1–9.

Penetrometer

Figure 1:
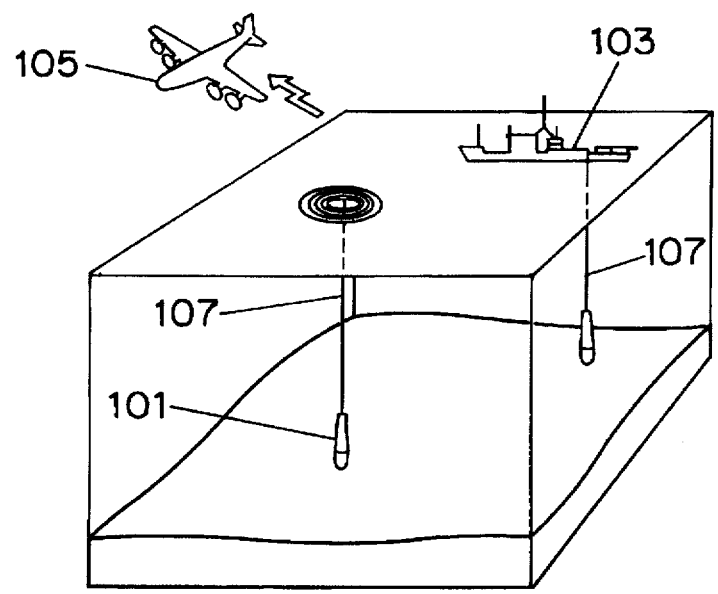
FIG. 1 is a pictorial illustration of the environment in which the invention is utilized.
Figure 2:
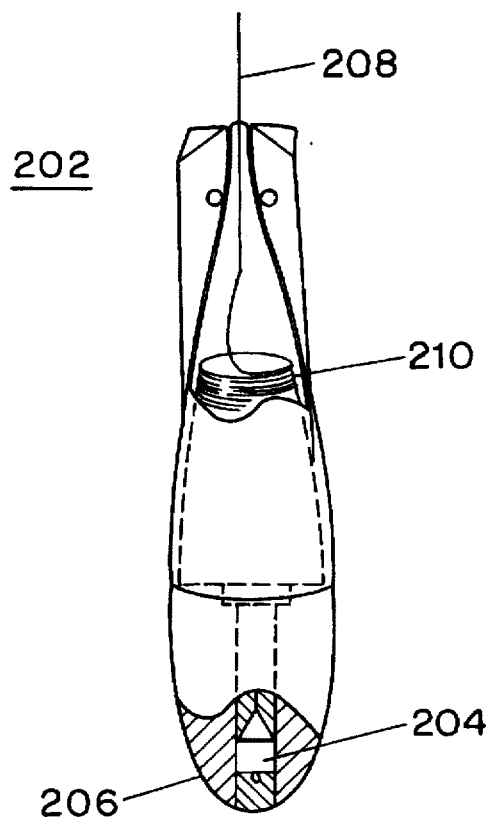
FIG. 2 is a cut away schematic of the penetrometer used in the preferred embodiment.

The dynamic penetrometer used in the preferred embodiment was designed to be deployed from an above surface platform, such as a moving ship or an aircraft, in the same manner as the expendable bathythermographs (XBT) that are currently in extensive use by the Navy and oceanographers to measure water temperature as a function of depth in the water column. FIG. 1 shows the environment in which the invention is used conceptually. The probes (101) are launched from a ship (103), airplane (105) or the like. For ship deployment, the probe remains attached to the ship platform. In the case of deployment from an airplane, the probe remains linked to a surface platform such as a buoy or float. The probes (101) are linked to the surface launching platform by thin wire (107) which simultaneously unreels from two coils, one mounted inside the probe and the other in a launching sleeve that remains aboard the launching platform. This two-coil configuration allows the probe to drop vertically without dragging the wire through the water while the launching platform moves away from the launch spot. A schematic of the probe is shown in FIG. 2. Standard XBT probes, whose general design is used in the preferred embodiment, are available from Sippicon, Inc. of Marian, Mass. In the XBT, water temperature is measured using a thermistor located near the probe tip in an annular cavity open to the water. After launch, the probe attains its terminal velocity and then drops vertically through the water at nearly constant speed, approximately 6.1 meters/second for a type T10 XBT, until it impacts the bottom.

In the dynamic penetrometer (XBP) used in the preferred embodiment (202), the thermistor of a type T10 XBT was replaced by a precision accelerometer (204) sealed into the tip of the probe (206) and the wire link (208) is used to carry a constant current loop to the electronics package which is an integral part of the accelerometer. This XBP with the accelerometer is available from Sippicon, Inc. for approximately $100 per unit. The coiled wire (210) is shown in the process of the deployment. During freefall and after the probe impacts the bottom, the wire remains intact so that signals from the accelerometer can be monitored over an extended period of time. The wire thus provides a means for transmitting the accelerometer signal representing the probe deceleration profile to the surface platform.

In the XBP, a probe with the same general shape as the XBT has been used for the dynamic penetrometer since it concentrates the force applied to the sediment to the nose cone and there is no side resistance along the tail section and fins. This greatly simplifies the interpretation of the impact signature when the probe penetrates a significant distance into the seafloor. FIG. 3 shows the general impact deceleration profiles for a granular material, such as sand, and a cohesive or plastic material such as clay. For the granular material the probe (301) cannot penetrate the material more than a few centimeters and the resulting deceleration signature shows a sharp spike (303). For the cohesive or plastic material the probe (305) is able to penetrate a significant distance into the material. The resulting deceleration profile (307) shows a much less marked deceleration as plastic deformation of the sediments occurs. In such cohesive materials, the probe may penetrate a foot or more.

When the probe initially impacts the seafloor, rapid deceleration occurs. FIG. 4 shows, in higher resolution, the expected deceleration signature as a function of time for an XBP probe. The full signature (402) shows an initial deceleration peak (404) followed by a period of damped oscillations (406). The initial part of the signal, which is roughly the shape of a half sine wave, corresponds to viscoplastic deformation of the sediment as the probe penetrates to a depth where there is no longer sufficient momentum to cause further permanent deformation. The remaining energy causes damped oscillations. The damped oscillations are shown in insert (408) and may be two or more orders of magnitude smaller in amplitude than the initial deceleration causing plastic deformation.

As will be detailed below, the frequency of these oscillations is related to the dynamic shear modulus of the sediment, while the maximum deceleration, or other profile parameters, may be used to determine the undrained shear strength. For the configuration shown in FIG. 2, the maximum deceleration can reach values of up to 250 g when the probe impacts a dense sand or it can be in the range of one or two g's in soft mud. When considering the damped oscillations, the amplitudes of acceleration are generally a small fraction of g. Hence the accelerometer, signal link. processing electronics and recording system must have a large enough dynamic range to allow analysis of the full impact signature and accurate determination of physical properties as diverse as undrained shear strength and dynamic shear modulus.

In addition, it is preferred to have the accelerometer, its mounting system and all other internal components of the probe free of resonances in the frequency range that will be excited by the fast rise time of the large amplitude pulses caused by impact on dilative granular materials. To prevent such resonances in the preferred embodiment the accelerometer was potted in an epoxy resin that fills the entire cavity of the nose cone. These resonances could be prevented by numerous techniques known to those skilled in the art, including, for example, attachment to a solid cone with a threaded stud or the use of rigid brackets.

Another preferred feature of the electronic system is that there be no spurious oscillations or "ringing." Such oscillations or ringing may result from the effects of processing the accelerometer signal using certain multipole filters when a shock-like pulse is processed. Oscillations of this kind can mask small scale mechanical oscillations of the penetrometer which are important in the analysis used to obtain dynamic shear modulus. This requires that anti-aliasing filters of the linear phase variety be used, such as the Bessel or Thompson type. Elimination of the spurious ringing ensures that small scale mechanical oscillations used to determine the dynamic shear modulus, as described below, will not be artificially contaminated by the electronic signal processing package.

Electronics and Data Acquisition

Figure 5:
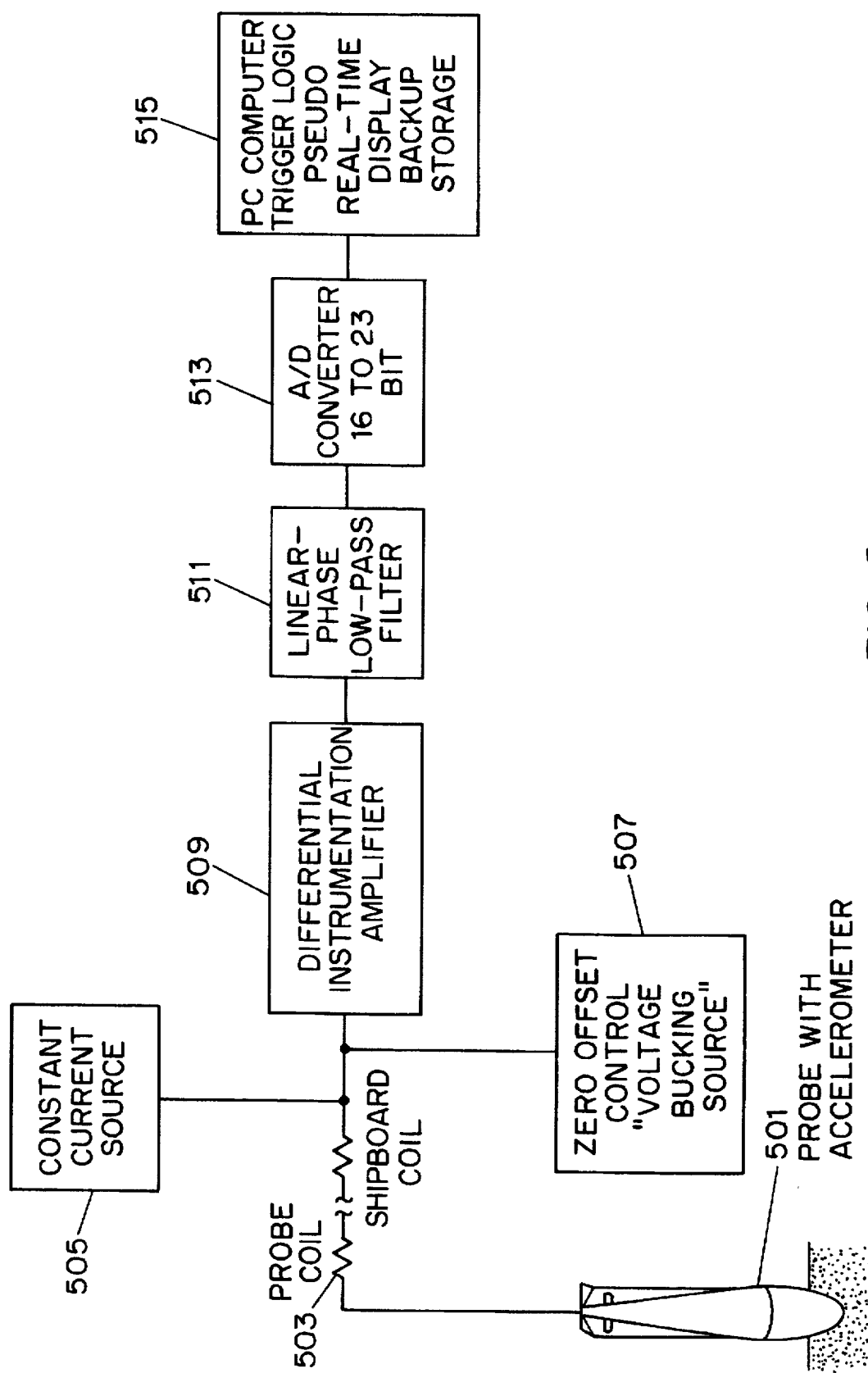
FIG. 5 is a block diagram representation of the data acquisition and signal processing components of the preferred embodiment.

FIG. 5 shows a schematic of the components required for data acquisition and processing for the preferred embodiment. An XBP containing a piezoelectric accelerometer (501) with an integral electronic circuit that allows both the power and the output signal to be transmitted on a single pair of wires deployed simultaneously from a probe coil (503) and a surface platform coil (505). This configuration eliminates the need for onboard batteries or extra wires in the connecting cable. The piezoelectric accelerometers used in the preferred embodiment are available from the PCB, Inc. of Depew, N.Y. The decelerometer used in the preferred embodiment was a type 321A70 from PCB, Inc. The units contain an electronics package that converts the high impedance output of the piezoelectric element into a low impedance output so that the voltage change across the unit is linearly related to the acceleration when a constant current is maintained in the two-wire loop linking the accelerometer to the power source. These units have a very long time constant (approximately 2 sec.) and therefore have very good low frequency response which avoids problems with signal distortion in the low amplitude portion of the signal following the initial shock.

A constant current source (505) supplies current to the data transmission wire and internal electronics of the accelerometer. In the preferred embodiment, an additional "voltage bucking source" (507) acts as a zero offset control that eliminates the DC bias that appears at the launcher end of the cable. The resulting signal with zero offset is fed into a precision instrumentation amplifier (509) with differential input that eliminates the common mode noise. In the preferred embodiment the signal is then anti-alias filtered with a linear phase low pass filter (511) of the type discussed above with a 1 kHz corner frequency and passed through an analog to digital converter (A/D converter) (513) that produces one or more digital signals with a total dynamic range of at least 16 bits to ensure sufficient resolution/dynamic range.

Numerous combinations of amplification and bit size can be used to attain the necessary dynamic range. For example, in the preferred embodiment a 12 bit A/D converter was used and the input signal was routed through two amplifiers, one with unity gain and the other with 30 dB of gain, thereby producing the desired 16 bit dynamic range. As an alternative, a 16 bit A/D converter and a single amplifier may be used. Other appropriate combinations will be apparent to those skilled in the art.

Output from the A/D converter is fed into a computer (515) which may store the data in several different file formats for later analysis. In the preferred embodiment the sampling rate of the A/D converter was 5 kHz. Using standard logic the computer detects bottom impact and can provide a pseudo real-time display of deceleration as a function of time for visual evaluation.

Data Analysis and Requisite Data Base

A computer program is used to scan the stored data to determine various characteristics of the probe impact and the deceleration profile. For example, the maximum deceleration may be determined, and the deceleration data may be integrated to obtain velocity and vertical position of the probe as a function of time. Further, the rate of change of deceleration (i.e., the jerk), the pulse width at various percentages of maximum amplitude, depth of probe penetration, total work done (i.e. area under deceleration versus time curve) and any other desired characteristics of the curve can be computed from the sampled data and used for analysis.

The final analysis used to quantify seafloor sediment characteristics such as the undrained shear strength and dynamic shear modulus depends on the development of a comprehensive data base based on insitu measurements. Such a data base will allow exploitation of relationships between information that is measurable by the dynamic penetrometer system described above, such as maximum deceleration, jerk, etc., and the basic insitu properties of the sediment. The derived relationships will allow determination of undrained shear strength and dynamic shear modulus from the dynamic penetrometer data. The insitu data base must be obtained for a consistent, unchanging set of penetrometer characteristics such as shape, mass, wire deployment method and impact velocity in order to provide the necessary link to the dynamically determined parameters that are markedly influenced by strain rate.

In the preferred embodiment the undrained shear strength, $S_u$, was determined by exploiting a known relationship between the quasi-static cone resistance, $Q_c$, and the undrained shear strength. The necessary data base for interpretation of the data from the penetrometer was obtained from an extensive set of insitu experiments wherein dynamic penetrometer tests and quasi-static cone penetrometer tests conforming to ASTM specifications were performed side by side at a wide variety of sites where the near-bottom sediments varied from soft mud to dense sand. At each site core or box samples were also obtained.

Figure 6:
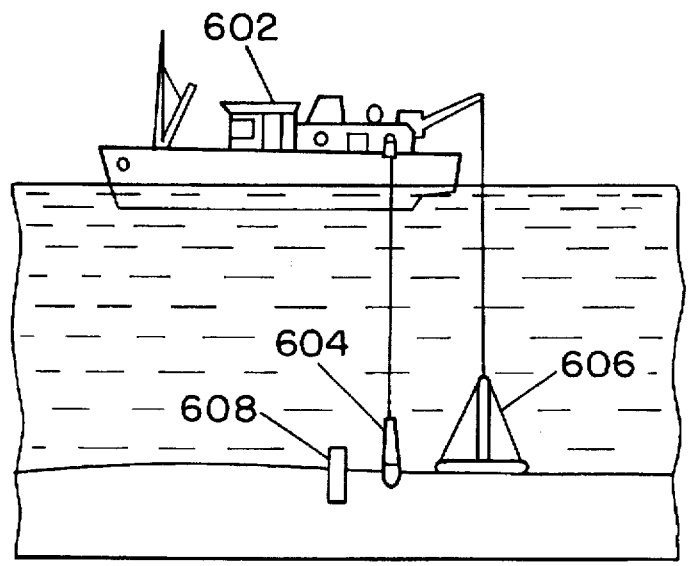
FIG. 6 is a pictorial illustration of the side by side insitu tests using the dynamic seafloor penetrometer and a standard quasi-static cone penetrometer from which the data base which correlates deceleration parameters and quasi-static cone resistance can be determined. The undrained shear strength can be calculated from the quasi-static cone resistance.

The experimental setup used in the preferred embodiment to obtain the insitu data base is shown schematically in FIG. 6. A ship born platform (602) allowed side by side comparisons of the dynamic penetrometer tests (604) and standard quasi-static cone penetrometer tests (606). Further, insitu core samples (608) were extracted for further analysis and comparison. The quasi-static, cone penetration tests were made using a special seafloor testing rig consisting of a heavily weighted, four-legged frame which supported the penetrometer driving mechanism and acted as a reaction to the force on the penetrating rod. In each test, a continuous record of penetration resistance was recorded until the probe had either penetrated 60 cm or the maximum allowable probe force was reached. A representative cone penetration resistance, $Q_c$, was then determined at the average depth of penetration of the dynamic penetrometers deployed at each site.

Figure 7:
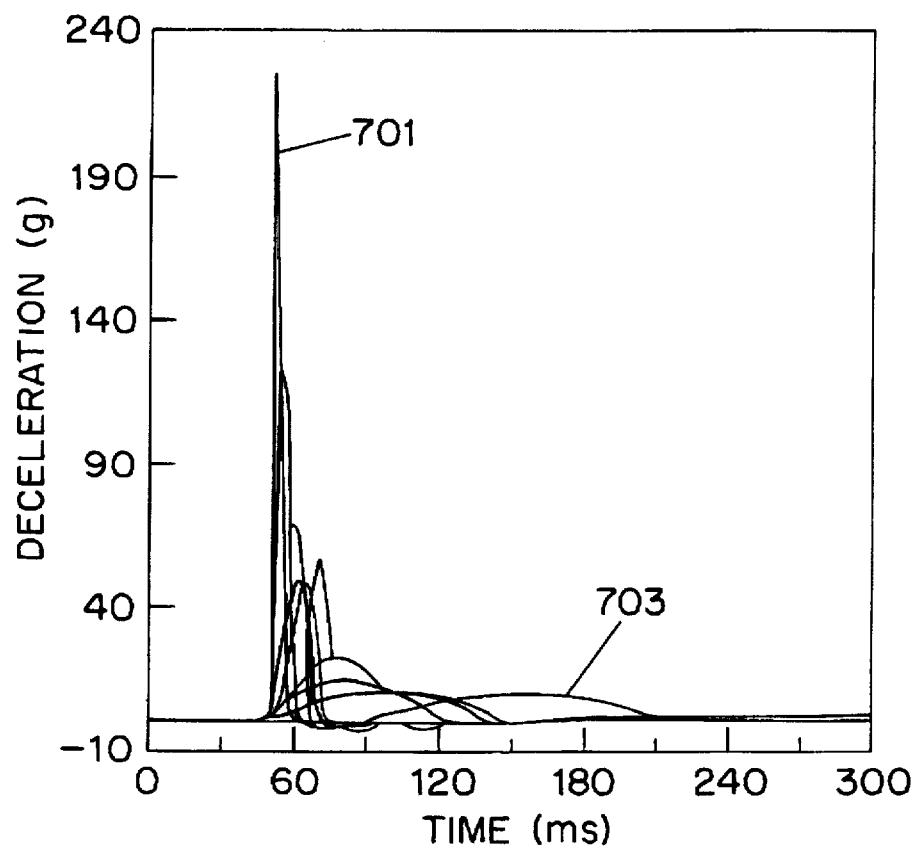
FIG. 7 is a composite plot of deceleration profiles for a variety of seafloor sediments ranging from dense granular sands to soft clays.

Typical results from the dynamic probe insitu tests are shown in FIG. 7. FIG. 7 is a composite plot showing the range of impact signatures (deceleration versus time) obtained from the dynamic tests. Those with high peak values of deceleration (greater than about 50 g's) and very fast rise times are characteristic of the dilative granular materials such as dense sands (701). The broadest profiles are characteristic of the softest clays (703). Sediments with intermediate properties fill the spectrum between these extremes.

Figure 8:
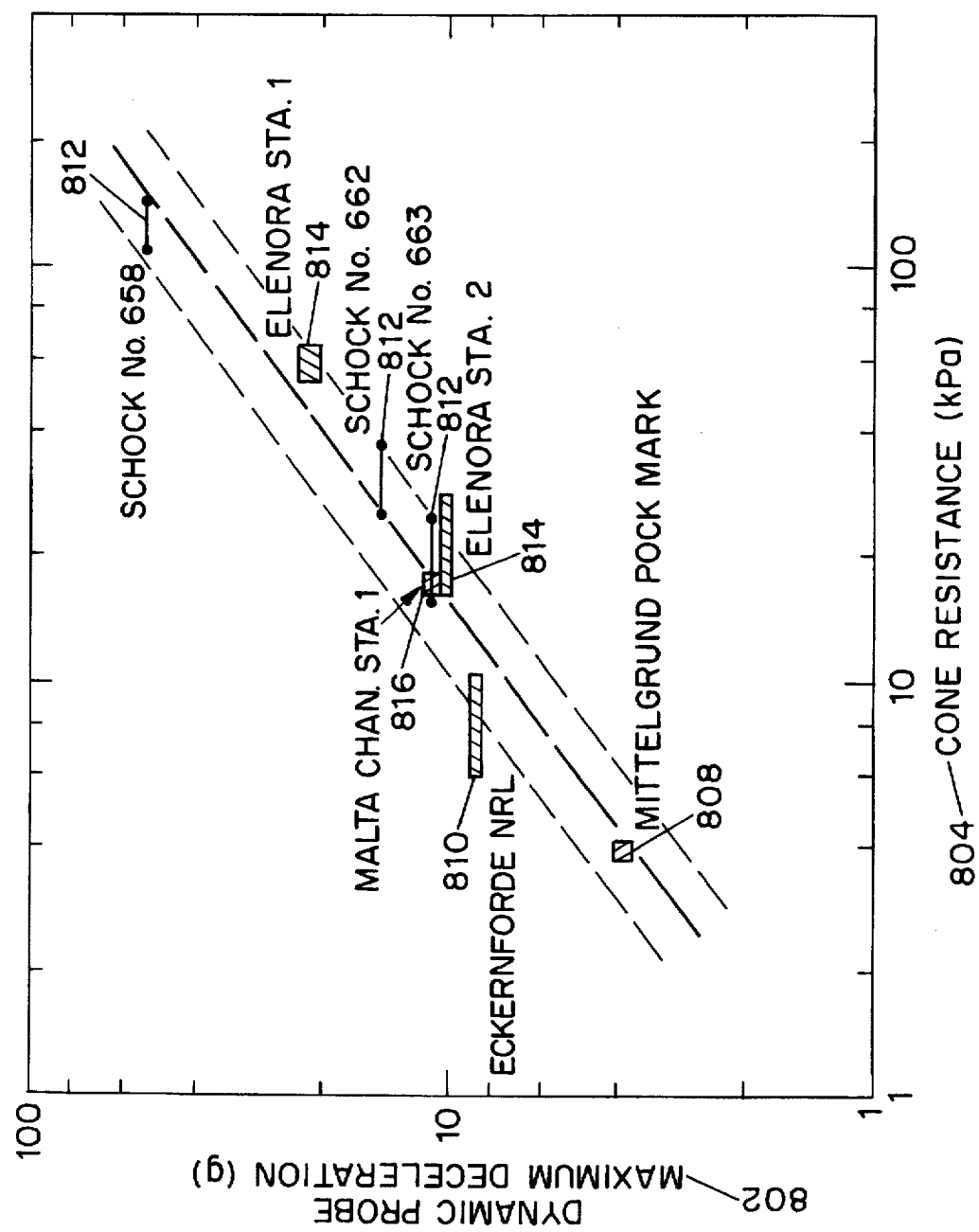
FIG. 8 is a log—log plot which shows the relationship between maximum deceleration of the dynamic penetrometer and quasi-static cone resistance from which the undrained shear strength may be derived. This data was obtained from insitu side by side tests using the dynamic seafloor penetrometer and the quasi-static cone penetrometer.

FIG. 8 is a summary graph of the side by side insitu test data that may be used to establish the relationship between the cone penetration resistance measured by the quasi-static cone penetrometer and maximum deceleration of the dynamic probe. The Mittelgrund (808), Eckernforde (810) and Schock (812) data points were based on side by side insitu quasi-static and dynamic measurements made in the Baltic Sea. The Elenora samples (814) were collected in the Adriatic Sea and the Malta Channel (816) data were collected in the Mediterranean Sea. The log of the maximum deceleration (802) for the dynamic penetrometer is shown plotted against the log of the quasi-static cone resistance (804). The link between the quasi-static cone resistance and the dynamic probe data was established by a least squares fit (806). The relationship for those cases where the sediment is primarily cohesive (i.e., maximum deceleration ≦ about 50 g's) is used to establish the relationship between dynamic response and undrained shear strength. Once known, this relationship can be exploited to determine quasi-static cone resistance based on dynamic penetrometer measurements at any location.

It should be noted that probes of a different shape, mass or terminal velocity will, of course, result in a different relationship. Accordingly, if probes other than the standard XBP type are used, new test data may be required to establish the linking relationship. Additionally, it has been found that a correlation between average jerk and quasi-static cone penetration will yield a relationship which may be used in a similar manner to the maximum deceleration versus cone penetration relationship. Those skilled in the art will find that numerous other parameters obtained from the dynamic probe, such as depth of penetration, will likewise provide the necessary link between dynamic and quasi-static measurements.

Undrained shear strength is related to cone resistance from the standard relationship $$Q_c = N_c \cdot S_u + \sigma_o$$

where $S_u$ is undrained shear strength, $\sigma_o$ is total overburden pressure (i.e., vertical stress due to weight of the overlying sediment) at the depth of the cone tip and $Q_c$ is the quasi-static cone resistance. $N_c$ is a constant derived from plasticity theory which depends on the geometry of the probe tip, surface conditions and similar factors. For our field tests we have determined the value to be 15 by computing the values of cone resistance from tests where the undrained shear strength was known from standard field and laboratory vane shear tests. For the small depths of penetration attained by the dynamic probe (3 to 25 cm), the average overburden pressure in the zone of penetration is small. Accordingly, $\sigma_o$ may either be neglected or estimated, based on an assumed sediment density that is consistent with the measured penetration resistance, without substantial error resulting in the derived value of the undrained shear strength.

Accordingly, with $N_c$ and $\sigma_o$ known, the disclosed invention makes it possible to determine the undrained shear strength, $S_u$, for cohesive materials from the deceleration profile of the XBP probe. The maximum deceleration, jerk, penetration depth or other measured quantity is correlated with a value of quasi-static cone resistance, $Q_c$, based on a relationship derived from the data base of insitu test results. Then by substitution into the above equation, the undrained shear strength, $S_u$, can be calculated.

The dynamic shear modulus of the sediment may be determined by the system and method disclosed by windowing the deceleration impact signal to exclude the initial pulse corresponding to plastic penetration. Fourier analysis is then performed on the remaining small scale oscillatory portion of the deceleration profile to determine the dominant frequency of damped vibration. The dominant or resonant frequency is then used to determine the dynamic shear modulus using solutions from the Theory of Elasticity for a vibrating rigid body at or near the surface of an elastic half space.

Figure 9A:
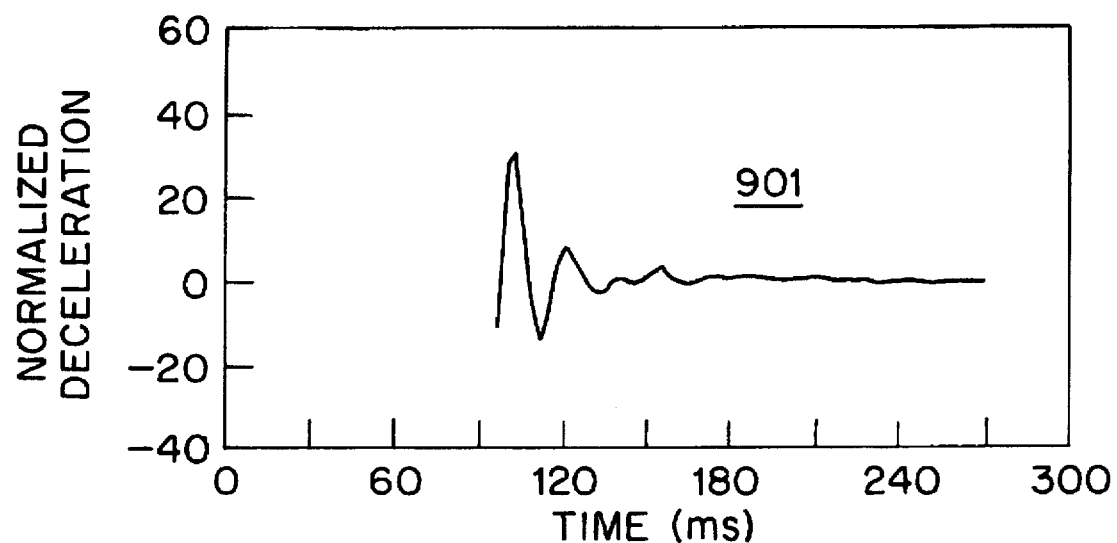
FIG. 9 is a graph of the damped oscillatory portion of the deceleration profile of the seafloor penetrometer and the Fourier amplitude spectrum of the oscillations. The dominant frequency allows the dynamic shear modulus to be calculated.
Figure 9B:
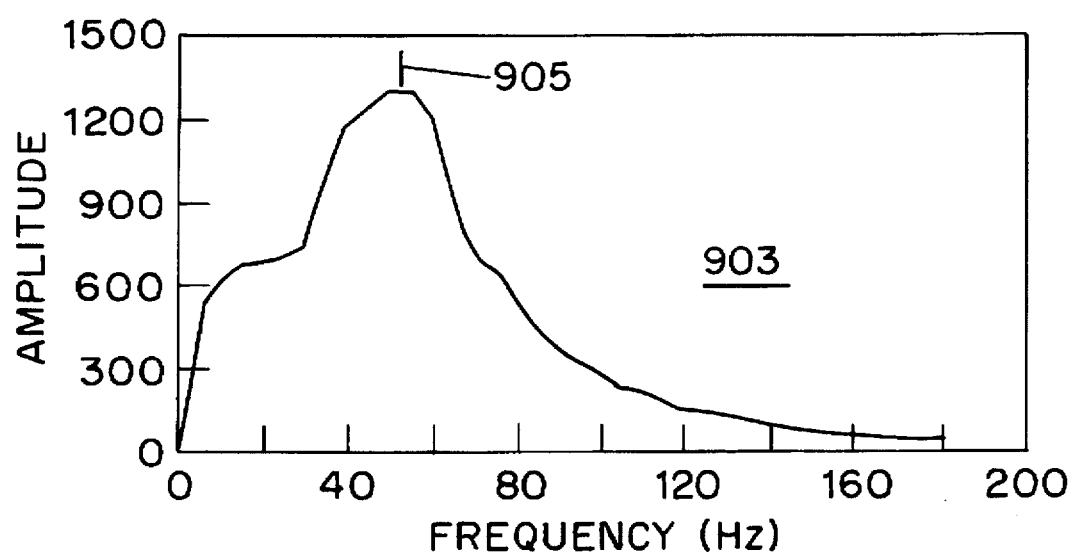

FIG. 9 shows the oscillations produced by a typical impact (901) after plastic deformation of the sediments has ended and the corresponding Fourier amplitude spectrum (903) from which the resonant frequency (905) is determined. This frequency together with information on the mass and geometry of the probe and the depth of penetration are used to solve for the dynamic shear modulus of the sediment using equations developed by geotechnical engineers for evaluating vibrations of footings embedded in soil.

In the equation below, the natural frequency of a cylindrical object of radius r embedded a distance d into the sediment is given by $$f_\kappa = \frac{1}{2\pi} \sqrt{\frac{G(r \cdot C_1 + d \cdot S_1)}{m}}$$

where m is the mass of the object, G is the dynamic shear modulus $C_1$ and $S_1$ are in general functions of frequency derived from the theory of elasticity. See, Novak, M. and Beredugo (1972) "Vertical Vibration of Embedded Footings," J. Soil Mech. and Found. Div. ASCE, 98, No. SM12, pp. 1291–1310.$C_1$ is based on the classical theory of Lamb (1904) which describes the response for a harmonic loading on the surface of an elastic half space and $S_1$ is based on the work of Baranov (1967) who considered the effects of embedment. See Baranov, V. A. (1967) "On the Calculation of Excited Vibrations of an Embedded Foundation (in Russian) Voprosy Dynamiki i Prochnocti, No. 14, Polytechnical Institute of Riga, pp. 195–209, and Lamb, H. (1904) "On the Propagation of Tremors Over the Surface of An Elastic Solid," Philosoph. Trans. Royal Soc., London, Ser. A, 203, pp. 1–42. Based on the work of Novak and Beredugo, precise values of $C_1$ and $S_1$ can be calculated, however, over a limited range of frequencies values $C_1$ and $S_1$ can be replaced by constants, 7.5 and 2.7 respectively, for good approximations to the precise analytical values. The above formula may thus be used to solve for the value of the dynamic shear modulus, given the results of an analysis such as that shown in FIG. 9 wherein the resonant frequency is determined from the peak in the Fourier amplitude spectrum.

While the invention has been described in terms of the foregoing specific embodiment, it will be apparent to those skilled in the art that various alterations and modifications may be made to the described embodiment without departing from the scope of the invention, as defined by the appended claims.

We claim:

1. An apparatus for determining undrained shear strength of seafloor sediments comprising,
    (a) a dynamic seafloor penetrometer that may be launched from an above surface platform and impacts the seafloor sediments at known terminal velocity and orientation;
    (b) an accelerometer mounted within the penetrometer capable of producing signals representative of a deceleration profile of the penetrometer as the penetrometer impacts and comes to rest in the seafloor sediment;
    (c) means for transmitting the signals representing the deceleration profile of the penetrometer to the above surface platform; and
    (d) a data base of insitu properties of seafloor sediments from which features of the penetrometer deceleration profile may be correlated to said properties, from which the undrained shear strength of the seafloor sediment impacted by the penetrometer may be determined, the data base being compiled from insitu side by side tests using the dynamic seafloor penetrometer and a standard quasi-static cone penetrometer, wherein the features of the deceleration profile are correlated to the sediment quasi-static cone resistance.

2. The apparatus of claim 1 wherein the surface platform is a ship or deployed from an airplane.

3. The apparatus of claim 1 wherein the feature of the deceleration profile is the penetrometer maximum deceleration, average jerk, maximum depth of penetration or work done as the penetrometer impacts the seafloor sediments, and the correlation is a least squares fit.

4. The apparatus of claim 1 wherein the means for transmitting the signals to the surface launching platform is a two wire data transmission line which is simultaneously uncoiled from a first reel mounted within the penetrometer and a second reel mounted on the surface launching platform, such that the penetrometer can drop vertically without dragging the data transmission wire through the water if the surface launch platform moves from the penetrometer launch point.

5. The apparatus of claim 4 wherein the accelerometer is piezoelectric with an integral electronic circuit that allows power and the deceleration profile signal to be transmitted on the two wire data transmission line.

6. The apparatus of claim 1 wherein the orientation of the penetrometer when it impacts the seafloor sediment is a nose cone down orientation, and the penetrometer has a geometric configuration that concentrates the force applied to the seafloor sediment to the nose cone such that there is minimal side resistance along a tail and fin section.

7. The apparatus of claim 1 wherein the penetrometer is free of resonances in a frequency range that will be excited by large amplitude pulses with fast rise times caused by impact of the penetrometer into the seafloor sediment.

8. An apparatus for determining dynamic shear modulus of seafloor sediments comprising, (a) a dynamic seafloor penetrometer that may be launched from an above surface platform and impacts the seafloor sediments at known terminal velocity and orientation;

(b) a two wire data transmission line for transmitting signals representing a deceleration profile of the penetrometer as the penetrometer impacts and comes to rest in the seafloor sediment to the above surface platform, which is simultaneously uncoiled from a first reel mounted within the penetrometer and a second reel mounted on the surface launching platform, such that the penetrometer can drop vertically without dragging the data transmission wire through the water if the surface launch platform moves from the penetrometer launch point;

(c) a piezoelectric accelerometer mounted within the penetrometer capable of producing the signals representative of the deceleration profile of the penetrometer with an integral electronic circuit that allows power and the deceleration profile signal to be transmitted on the two wire data transmission line, wherein the integral electronic circuit converts high impedance output of the piezoelectric accelerometer to low impedance output so that voltage change across the accelerometer is linearly related to acceleration when a constant current is maintained in the two wire line; and (d) means to analyze the deceleration profile wherein a damped oscillatory portion of the deceleration profile may be separated from an initial portion of the deceleration profile wherein permanent plastic deformation of seafloor sediment is caused, and the dynamic shear modulus can be calculated based on a dominant frequency of the damped oscillatory portion of the deceleration profile.

9. The apparatus of claim 8 wherein the surface platform is a ship or deployed from an airplane.

10. The apparatus of claim 8 further comprising:

(a) a constant current source which supplies current to the data transmission line and the integral electronic circuit of the accelerometer;

(b) a zero offset control that eliminates any DC bias that appears at the launch platform end of the data transmission line;

(c) a precision instrumentation amplifier with differential input that eliminates common mode noise;

(d) an anti-alias low pass filter that avoids masking low amplitude signals; and (e) an analog to digital converter to transform the signal into a form usable by digital computers.

11. The apparatus of claim 8 wherein the accelerometer has a long time constant and sufficiently low frequency response to avoid masking, due to signal distortion, of the damped oscillatory portion of the profile.

12. The apparatus of claim 8 wherein the orientation of the penetrometer when it impacts the seafloor sediment is a nose cone down orientation, and the penetrometer has a geometric configuration that concentrates the force applied to the seafloor sediment to the nose cone such that there is minimal side resistance along a tail and fin section.

13. The apparatus of claim 8 wherein the dominant frequency is determined by calculating the Fourier spectrum of the damped oscillatory portion of the deceleration profile.

14. A method for determining undrained shear strength of seafloor sediments comprising, (a) launching a dynamic seafloor penetrometer from an above surface platform such that said penetrometer impacts the seafloor sediments at known terminal velocity and orientation;

(b) producing signals representative of a deceleration profile of the penetrometer as the penetrometer impacts and comes to rest within the seafloor sediment, said signals being produced by an accelerometer mounted within the penetrometer;

(c) transmitting the signals from the penetrometer to the above surface platform;

(d) compiling a data base of insitu properties of seafloor sediments from which features of the penetrometer deceleration profile may be correlated to said properties, the data base being compiled from insitu side by side tests using the dynamic seafloor penetrometer and a standard quasi-static cone penetrometer; and (e) correlating the features of the penetrometer deceleration profile to the sediment quasi-static cone resistance from which the undrained shear strength can be determined.

15. The method of claim 14 wherein the surface platform is a ship or deployed from an airplane.

16. The method of claim 14 wherein the feature of the deceleration profile is the penetrometer maximum deceleration, average jerk, maximum depth of penetration or work done as the penetrometer impacts the seafloor sediments, and the correlation is a least squares fit.

17. The method of claim 14 wherein the means for transmitting the signals to the surface launching platform is a two wire data transmission line which is simultaneously uncoiled from a first reel mounted within the penetrometer and a second reel mounted on the surface launching platform, such that the penetrometer can drop vertically without dragging the data transmission wire through the water if the surface launch platform moves from the penetrometer launch point.

18. The method of claim 17 wherein the accelerometer is piezoelectric with an integral electronic circuit that allows power and the deceleration profile signal to be transmitted on the two wire data transmission line.

19. The method of claim 14 wherein the orientation of the penetrometer when it impacts the seafloor sediment is a nose cone down orientation, and the penetrometer has a geometric configuration that concentrates the force applied to the seafloor sediment to the nose cone such that there is minimal side resistance along a tail and fin section.

20. The method of claim 14 wherein the penetrometer is free of resonances in a frequency range that will be excited by large amplitude pulses with fast rise times caused by impact of the penetrometer into the seafloor sediment.

21. A method for determining dynamic shear modulus of seafloor sediments comprising,
   (a) launching a dynamic seafloor penetrometer from an above surface platform such that said penetrometer impacts the seafloor sediments at known terminal velocity and orientation;
   (b) producing signals representative of a deceleration profile of the penetrometer as the penetrometer impacts and comes to rest within the seafloor sediment, said signals being produced by an accelerometer mounted within the penetrometer;
   (c) transmitting the signals from the penetrometer to the above surface platform;
   (d) separating a damped oscillatory portion of the deceleration profile from an initial portion of the deceleration profile wherein permanent plastic deformation of seafloor sediment is caused;
   (e) determining a dominant frequency of the damped oscillatory portion of the deceleration profile; and
   (f) calculating the dynamic shear modulus from the dominant frequency.

22. The method of claim 21 wherein the surface platform is a ship or deployed from an airplane.

23. The method of claim 21 wherein the means for transmitting the signals to the surface launching platform is a two wire data transmission line which is simultaneously uncoiled from a first reel mounted within the penetrometer and a second reel mounted on the surface launching platform, such that the penetrometer can drop vertically without dragging the data transmission wire through the water if the surface launch platform moves from the penetrometer launch point.

24. The method of claim 22 wherein the accelerometer is piezoelectric with an integral electronic circuit that allows power and the deceleration profile signal to be transmitted on the two wire data transmission line.

25. The method of claim 23 wherein the integral electronic circuit converts high impedance output of the piezoelectric accelerometer to low impedance output so that voltage change across the accelerometer is linearly related to acceleration when a constant current is maintained in the two wire line.

26. The method of claim 24 further comprising:
   (a) supplying current to the data transmission line and the integral electronic circuit of the accelerometer using a constant current source;
   (b) eliminating any DC bias that appears at the launch platform end of the data transmission line using a zero offset control;
   (c) eliminating common mode noise using a precision instrumentation amplifier with differential input;
   (d) avoiding masking low amplitude signals using an anti-alias low pass filter; and
   (e) transforming the signal into a form usable by digital computers using an analog to digital converter.

27. The method of claim 24 wherein the accelerometer has a long time constant and sufficiently low frequency response to avoid masking, due to signal distortion, of the damped oscillatory portion of the profile.

28. The method of claim 20 wherein the orientation of the penetrometer when it impacts the seafloor sediment is a nose cone down orientation, and the penetrometer has a geometric configuration that concentrates the force applied to the seafloor sediment to the nose cone such that there is minimal side resistance along a tail and fin section.

29. The method of claim 20 wherein the dominant frequency is determined by calculating the Fourier spectrum of the damped oscillatory portion of the deceleration profile.

30. An apparatus for determining undrained shear strength of seafloor sediments comprising,
   (a) a dynamic seafloor penetrometer that may be launched from an above surface platform and impacts the seafloor sediments at known terminal velocity and orientation;
   (b) a two wire data transmission line for transmitting signals representing a deceleration profile of the penetrometer as the penetrometer impacts and comes to rest in the seafloor sediment to the above surface platform which is simultaneously uncoiled from a first reel mounted within the penetrometer and a second reel mounted on the surface launching platform, such that the penetrometer can drop vertically without dragging the data transmission wire through the water if the surface launch platform moves from the penetrometer launch point; and
   (c) a piezoelectric accelerometer mounted within the penetrometer capable of producing the signals representative of the deceleration profile of the penetrometer, said accelerometer having an integral electronic circuit that allows power and the deceleration profile signal to be transmitted on the two wire data transmission line wherein the integral electronic circuit converts high impedance output of the piezoelectric accelerometer to low impedance output so that voltage change across the accelerometer is linearly related to acceleration when a constant current is maintained in the two wire line;
   (d) a data base of insitu properties of seafloor sediments from which features of the penetrometer deceleration profile may be correlated to said properties, from which the undrained shear strength of the seafloor sediment impacted by the penetrometer may be determined.

31. The apparatus of claim 30 further comprising:
   (a) a constant current source which supplies current to the data transmission line and the integral electronic circuit of the accelerometer;
   (b) a zero offset control that eliminates any DC bias that appears at the launch platform end of the data transmission line;
   (c) a precision instrumentation amplifier with differential input that eliminates common mode noise;
   (d) an anti-alias low pass filter that avoids masking low amplitude signals; and
   (e) an analog to digital converter to transform the signal into a form usable by digital computers.

32. A method for determining undrained shear strength of seafloor sediments comprising,
   (a) launching a dynamic seafloor penetrometer from an above surface platform such that said penetrometer impacts the seafloor sediments at known terminal velocity and orientation;

(b) producing signals representative of a deceleration profile of the penetrometer as the penetrometer impacts and comes to rest within the seafloor sediment, said signals being produced by a piezoelectric accelerometer mounted within the penetrometer with an integral electronic circuit that allows power and the deceleration profile signal to be transmitted on a two wire data transmission line wherein the integral electronic circuit converts high impedance output of the piezoelectric accelerometer to low impedance output so that voltage change across the accelerometer is linearly related to acceleration when a constant current is maintained in the two wire line;

(c) transmitting the signals from the penetrometer to the above surface platform using a two wire data transmission line which is simultaneously uncoiled from a first reel mounted within the penetrometer and a second reel mounted on the surface launching platform, such that the penetrometer can drop vertically without dragging the data transmission wire through the water if the surface launch platform moves from the penetrometer launch point;

(d) compiling a data base of insitu properties of seafloor sediments from which features of the penetrometer deceleration profile may be correlated to said properties; and (e) correlating the features of a penetrometer deceleration profile with properties of seafloor sediments and determining the undrained shear strength from the penetrometer deceleration profile.

33. The method of claim 32 further comprising:

(a) supplying current to the data transmission line and the integral electronic circuit of the accelerometer using a constant current source;

(b) eliminating any DC bias that appears at the launch platform end of the data transmission line using a zero offset control;

(c) eliminating common mode noise using a precision instrumentation amplifier with differential input;

(d) avoiding masking low amplitude signals using an anti-alias low pass filter; and (e) transforming the signal into a form usable by digital computers using an analog to digital converter.

34. An apparatus for determining undrained shear strength of seafloor sediments comprising, (a) a dynamic seafloor penetrometer that may be launched from an above surface platform and impacts the seafloor sediments at known terminal velocity and orientation wherein the orientation of the penetrometer when it impacts the seafloor sediment is a nose cone down orientation, the nose cone portion impacting the sea floor and the penetrometer has a geometric configuration that concentrates the force applied to the seafloor sediment to the nose cone such that there is minimal side resistance along a tail and fin section the tail and fin section having a diameter less than the nose section;

(b) an accelerometer mounted within the penetrometer capable of producing signals representative of a deceleration profile of the penetrometer as the penetrometer impacts and comes to rest in the seafloor sediment;

(c) means for transmitting the signals representing the deceleration profile of the penetrometer to the above surface platform; and (d) a data base of insitu properties of seafloor sediments from which features of the penetrometer deceleration profile may be correlated to said properties, wherein the undrained shear strength of the seafloor sediment impacted by the penetrometer is determined.

35. An apparatus for determining dynamic shear modulus of seafloor sediments comprising, (a) a dynamic seafloor penetrometer that may be launched from an above surface platform and impacts the seafloor sediments at known terminal velocity and orientation wherein the orientation of the penetrometer when it impacts the seafloor sediment is a nose cone down orientation, the nose cone portion impacting the sea floor and the penetrometer has a geometric configuration that concentrates the force applied to the seafloor sediment to the nose cone such that there is minimal side resistance along a tail and fin section;

(b) an accelerometer mounted within the penetrometer capable of producing signals representative of a deceleration profile of the penetrometer as the penetrometer impacts and comes to rest in the seafloor sediment;

(c) means for transmitting the signals representing the deceleration profile of the penetrometer to the above surface platform; and (d) means to analyze the deceleration profile wherein a damped oscillatory portion of the deceleration profile may be separated from an initial portion of the deceleration profile wherein permanent plastic deformation of seafloor sediment is caused, and the dynamic shear modulus can be calculated based on a dominant frequency of the damped oscillatory portion of the deceleration profile.

* * * * *

UNITED STATES PATENT AND TRADEMARK OFFICE
CERTIFICATE OF CORRECTION

PATENT NO. : 5,681,982
DATED : October 28, 1997
INVENTOR(S) : Robert D. Stoll, et al.

It is certified that error appears in the above-indentified patent and that said Letters Patent is hereby corrected as shown below:

Title page, Item [56], eighth line, "4,593,895 6/1986" should read --5,493,895 2/1996--. Col. 3, line 36, "it's" should read -- its --. Col. 8, line 28, "born" should read -- borne --. Col. 13, line 37 of claim 23, "claim 21" should read --claim 22--; line 46 of claim 24, "claim 22" should read --claim 23--; line 50 of claim 25, "claim 23" should read -- claim 24-- ; line 1 of claim 56, "claim 24" should read --claim 25--. Col. 14, line 3 of claim 27, "claim 24" should read -- claim 25--; line 7 of claim 28, "claim 20" should read -- claim 21--; line 13 of claim 29,"claim 20" should read --claim 21--.

Signed and Sealed this

Twenty-first Day of July, 1998

Attest:

BRUCE LEHMAN

*Attesting Officer*  *Commissioner of Patents and Trademarks*